(12) United States Patent
Pi Subirana et al.

(10) Patent No.: US 6,710,082 B1
(45) Date of Patent: Mar. 23, 2004

(54) USE OF HYDROXYCARBOXYLIC ACID ESTERS AS THICKENERS

(75) Inventors: Rafael Pi Subirana, Granollers (ES); Ester Prat Queralt, Calella (ES); Joaquim Bigorra Llosas, Sabadell (ES)

(73) Assignee: Cognis Deutschland GbmH & Co. KG, Duesseldorf (DE)

( * ) Notice: Subject to any disclaimer, the term of this patent is extended or adjusted under 35 U.S.C. 154(b) by 452 days.

(21) Appl. No.: 09/194,824

(22) PCT Filed: May 22, 1997

(86) PCT No.: PCT/EP97/02619

§ 371 (c)(1),
(2), (4) Date: May 25, 1999

(87) PCT Pub. No.: WO97/46653

PCT Pub. Date: Dec. 11, 1997

(30) Foreign Application Priority Data

Jun. 3, 1996 (DE) .......................................... 196 22 214

(51) Int. Cl.[7] .......................... A61K 31/185; C11D 1/74
(52) U.S. Cl. ........................ 514/553; 514/723; 514/738; 424/70.28; 424/70.31; 424/401; 510/434; 554/227; 554/213; 554/219
(58) Field of Search .......................... 510/434; 554/227, 554/213, 219; 514/723, 738, 553; 424/70.28, 70.31, 401

(56) References Cited

U.S. PATENT DOCUMENTS

| | | | |
|---|---|---|---|
| 3,547,828 A | 12/1970 | Mansfield | 252/351 |
| 3,707,535 A | 12/1972 | Lew | 260/210 R |
| 3,772,269 A | 11/1973 | Lew | 260/210 R |
| 3,839,318 A | 10/1974 | Mansfield | 260/210 R |
| 4,172,887 A | 10/1979 | Vanlerberghe et al. | 424/70 |
| 4,349,669 A | 9/1982 | Klahr et al. | 536/127 |
| 4,614,622 A | 9/1986 | Huettinger et al. | 260/410.7 |
| 5,034,159 A | 7/1991 | Tesmann et al. | 252/551 |
| 5,302,377 A | 4/1994 | Pereira et al. | 424/59 |
| 5,576,451 A | 11/1996 | Trius Oliva et al. | 554/227 |

FOREIGN PATENT DOCUMENTS

| | | |
|---|---|---|
| DE | 11 65 574 | 3/1964 |
| DE | 19 43 689 | 3/1970 |
| DE | 20 36 472 | 2/1971 |
| DE | 30 01 064 | 7/1981 |
| DE | 20 24 051 | 5/1986 |
| DE | 38 17 415 | 11/1989 |
| DE | 41 37 317 | 5/1993 |
| EP | 0 077 167 | 4/1983 |
| EP | 0 199 131 | 10/1986 |
| FR | 2 252 840 | 12/1978 |
| FR | 2 534 923 | 4/1984 |
| FR | 2 623 422 | 5/1989 |
| GB | 962 919 | 7/1964 |
| GB | 1 333 475 | 10/1973 |

OTHER PUBLICATIONS

J. Falbe "Surfactants in Consumer Products", Springer Verlag, Berlin, (1987) pp. 54–124.
J. Falbe "Katalysatoren, Tenside und Mineraloeladditive" Thieme Verlag, Stuttgart, (1978), pp. 123–217.
"Kosmetische Faerbemittel", Farbstoffkommission der Deutschen Forschungsgemeinschaft, Verlag Chemie, Weinheim, (1984), pp. 81–106.

*Primary Examiner*—Russell Travers
*Assistant Examiner*—Shahnam Sharareh
(74) *Attorney, Agent, or Firm*—John E. Drach; Steven J. Trzaska

(57) ABSTRACT

A thickener composition containing a reaction product of a hydroxycarboxylic acid selected from the group consisting of tartaric acid, malic acid, citric acid and mixtures thereof, and a fatty alcohol polyglycol ether corresponding to formula I:

$$R^1O(CH_2CH_2O)_nH \qquad (I)$$

wherein $R^1$ is an alkyl and/or alkenyl group containing from 6 to 22 carbon atoms, and n is a number from 20 to 150.

5 Claims, No Drawings

USE OF HYDROXYCARBOXYLIC ACID ESTERS AS THICKENERS

BACKGROUND OF THE INVENTION

This invention relates to the use of hydroxycarboxylic acid esters obtained by reaction of selected hydroxycarboxylic acids in known manner with selected hydroxyl compounds as thickeners for the production of surface-active formulations.

Surface-active formulations such as, for example, manual dishwashing detergents or hair shampoos, liquid detergents or shower gels are more or less concentrated aqueous surfactant preparations that are all expected to have a viscosity which, on the one hand, is low enough to ensure problem-free handling by the user but which, on the other hand, is also high enough to allow economical use. For preparations which are actually marketed in their in-use concentration and which do not have to be diluted by the user at all before use, this means that the water-thin surfactant solutions have to be adjusted to a relatively high viscosity. In many cases, this is done by the addition of electrolyte salts or polymers. However, in critical cases, including for example anionic surfactants containing internal polar groups and, in particular, sugar surfactants of the alkyl glucoside type, this measure is unsuccessful. Thus, the viscosity of alkyl glucoside solutions, for example, can be distinctly reduced by addition of sodium chloride.

Numerous thickeners with which the viscosity of the "problematical" surfactants mentioned above can be controlled to a greater or lesser extent are known from the prior art. One example of a suitable thickener are the narrow-range fatty alcohol polyglycol ethers known from German patent application DE-A1 3817415 (Henkel). Other suitable thickeners, namely highly ethoxylated glycerol esters, are proposed in German patent application DE-A1 4137317 (Henkel) and in French patent application FR-A 2534923 (Th. Goldschmidt). Esters of citric acid with fatty alcohols are known, for example, from French patent application FR-A 2623422 (L'Oréal). However, it has been found in practice that these thickeners do not produce an adequate or sufficiently stable increase in viscosity so that there is still a need for improved thickeners for the production of surface-active formulations.

Accordingly, the problem addressed by the present invention was to provide thickeners which would even enable aqueous solutions of "problematical" surfactants to be reliably and permanently thickened without adversely affecting the performance properties of the preparations. At the same time, the products would show excellent ecotoxicological compatibility.

DESCRIPTION OF THE INVENTION

The present invention relates to the use of hydroxycarboxylic acid esters which are obtained by reacting hydroxycarboxylic acids selected from the group consisting of tartaric acid, malic acid and citric acid with fatty alcohol polyglycol ethers corresponding to formula (I):

$$R^1O(CH_2CH_2O)_nH \quad (I)$$

in which $R^1$ is an alkyl and/or alkenyl group containing 6 to 22 carbon atoms and n is a number of 20 to 150, by methods known per se as thickeners for the production of surface-active formulations.

It has surprisingly been found that the new esters have a strong thickening effect in aqueous surfactant solutions so that a sufficiently high and stable viscosity can even be adjusted in systems that are difficult to thicken, such as for example sugar surfactants of the alkyl glucoside or fatty acid-N-methyl glucamide type. Another advantage of this group of thickeners is that they show high ecotoxicological compatibility and may readily be incorporated in cosmetic or pharmaceutical preparations both in hot and in cold conditions.

Hydroxycarboxylic Acids

Suitable hydroxycarboxylic acids are tartaric acid, malic acid and, in particular, citric acid which may be used in water-free form, but which preferably contain water of crystallization.

Fatty Alcohol Polyglycol Ethers

Fatty alcohol polyglycol ethers which may be used as starting materials for the purposes of the present invention are commercially available addition products of, on average, 20 to 150, preferably 30 to 120 and more preferably 40 to 100 moles of ethylene oxide with technical fatty alcohols containing 6 to 22, preferably 12 to 18 and more preferably 16 to 18 carbon atoms. Typical examples are the corresponding ethoxylates of caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, eleaostearyl alcohol, arachyl alcohol, gadoleyl alcohol, behenyl alcohol, erucyl alcohol and brassidyl alcohol and technical mixtures thereof. Adducts of 40 to 100 moles of ethylene oxide with cetearyl alcohol, tallow fatty alcohol or palm oil alcohol are preferably used.

In overall terms, hydroxycarboxylic acid esters derived from citric acid and fatty alcohol polyglycol ethers corresponding to formula (I), in which $R^1$ is a $C_{16-18}$ alkyl group and n is a number of 40 to 100, are preferred.

Esterification

The esterification of the hydroxycarboxylic acids with the fatty alcohol polyglycol ethers may be carried out in known manner. It is advisable to carry out the reaction in the presence of an acidic catalyst, for example methane sulfonic acid or p-toluene sulfonic acid, which may be used in quantities of 0.1 to 1% by weight and preferably in quantities of 0.2 to 0.7% by weight, based on the starting materials. In addition, to improve the color quality of the reaction products, it has proved to be of advantage to use a reducing agent, for example hypophosphorous acid or sodium hypophosphite, which should be used in a quantity of about 1 to 50% by weight, based on the catalyst. The hydroxycarboxylic acids and the polyglycol ethers are generally used in quantities which correspond to a molar ratio of carboxyl to hydroxyl groups of 1:1 to 3:1 and preferably 2:1 to 2.5:1. The esterification reaction is carried out at temperatures of 100 to 200° C., preferably under reduced pressure. In the case of water-soluble products, the progress of the reaction can be followed via the parameters of acid value and viscosity. The esterification reaction is normally continued until the acid value has fallen to a value below 20 and preferably to a value below 10. However, it is important in this regard to bear in mind that esters with the same acid value can have very different thickening effects. Esters with particularly favorable properties are obtained not only when they meet the low acid value requirement, but also when a 5% by weight sample of the ester in water has a Brookfield viscosity of at least 2,000 mPas, preferably of at least 4,000 mPas and more preferably of at least 7,000 mPas. To produce these preferred esters, heating of the reaction products is continued until a sample shows the required viscosity.

The esters have strong thickening properties and are therefore suitable as thickeners for the production of aqueous surface-active formulations, of which typical examples are liquid detergents, manual dishwashing detergents, fabric softeners and, in particular, cosmetic and pharmaceutical preparations, for example hair shampoos, shower gels, foam baths, hair conditioners, skin lotions, cremes, emollients and the like.

Surfactants

The formulations mentioned above may contain anionic, nonionic, cationic and/or amphoteric or zwitterionic surfactants as further components. Typical examples of anionic surfactants are alkylbenzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, proteinfatty acid condensates (more particularly wheat-based vegetable products) and alkyl(ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, fatty acid N-alkyl glucamides, protein hydrolyzates (more particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217. The new esters are preferably used for thickening aqueous surfactant solutions containing alkyl and/or alkenyl oligoglycosides, fatty acid-N-alkyl glucamides, fatty alcohol ether sulfates, sulfosuccinates, betaines and/or esterquats.

Auxiliaries and Additives

If the new esters are used as thickeners for cosmetic or pharmaceutical formulations, for example hair or skin treatment formulations, the formulations in question may contain oils, emulsifiers, superfatting agents, stabilizers, waxes, consistency regulators, co-thickeners, cationic polymers, silicone compounds, biogenic agents, antidandruff agents, film formers, preservatives, hydrotropes, solubilizers, UV filters, insect repellents, self-tanning agents, dyes and fragrances as further auxiliaries and additives.

Suitable oils are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, esters of $C_{6-22}$ fatty alcohols and/or Guerbet alcohols with aromatic carboxylic acids, more particularly benzoic acid, vegetable oils, branched primary alcohols, substituted cyclohexanes, linear $C_{6-22}$ fatty alcohol carbonates, Guerbet carbonates, dialkyl ethers, silicone oils and/or aliphatic or naphthenic hydrocarbons.

Suitable emulsifiers are, for example, nonionic surfactants from at least one of the following groups:

(1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group;

(2) $C_{12/18}$ fatty acid monoesters and diesters of adducts of 1 to 30 moles of ethylene oxide with glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) adducts of 15 to 60 moles of ethylene oxide with castor oil and/or hydrogenated castor oil;

(6) polyol esters and, in particular, polyglycerol esters such as, for example, polyglycerol polyricinoleate or polyglycerol poly-12-hydroxystearate. Mixtures of compounds from several of these classes are also suitable;

(7) adducts of 2 to 15 moles of ethylene oxide with castor oil and/or hydrogenated castor oil;

(8) partial esters based on linear, branched, unsaturated or saturated $C_{12/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) trialkyl phosphates and mono-, di- and/or tri-PEG-alkyl phosphates;

(10) wool wax alcohols;

(11) polysiloxane/polyalkyl polyether copolymers and corresponding derivatives;

(12) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol, and

(13) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

$C_{8/18}$ alkyl mono- and oligoglycosides, their production and their use as surfactants are known, for example, from U.S. Pat. No. 3,839,318, U.S. Pat. No. 3,707,535, U.S. Pat. No. 3,547,828, DE-OS 19 43 689, DE-OS 20 36 472 and DE-A1 30 01 064 and also from EP-A 0 077 167. They are produced in particular by reacting glucose or oligosaccharides with primary $C_{8/18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example coco-acylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Coco-amidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine. Besides ampholytic emulsifiers, quaternary emulsifiers may also be used, those of the esterquat type, especially methyl-quaternized difatty acid triethanolamine ester salts, being particularly preferred.

The superfatting agents used may be such substances as, for example, lanolin and lecithin and polyethoxylated or acylated lanolin and lecithin derivatives, polyol fatty acid esters, monoglycerides and fatty acid alkanolamides, the latter also serving as foam stabilizers. Suitable consistency regulators are, above all, fatty alcohols containing 12 to 22 and preferably 16 to 18 carbon atoms and, in addition, partial glycerides. These substances are preferably used in combination with alkyl oligoglucosides and/or fatty acid-N-methyl glucamides of the same chain length and/or polyglycerol poly-12-hydroxystearates. Suitable co-thickeners are, for example, polysaccharides, more particularly xanthan gum, guar guar, agar agar, alginates and tyloses, carboxymethyl cellulose and hydroxyethyl cellulose, relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols such as, for example, pentaerythritol or trimethylol propane, narrow-range fatty alcohol ethoxylates or alkyl oligoglucosides and electrolytes such as sodium chloride and ammonium chloride.

Suitable cationic polymers are, for example, cationic cellulose derivatives such as, for example, the quaternized hydroxyethyl cellulose available under the name of Polymer JR 400® from Amerchol, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat®L Grünau), quaternized wheat polypeptides, polyethyleneimine, cationic silicone polymers such as, for example, Amidomethicone, copolymers of adipic acid and dimethyl aminohydroxypropyl diethylenetriamine (Cartaretine®, Sandoz), copolymers of acrylic acid with dimethyl diallyl ammonium chloride (Merquat® 550, Chemviron), polyamino-polyamides as described, for example, in FR-A 2252840 and crosslinked water-soluble polymers thereof, cationic chitin derivatives such as, for example, quaternized chitosan, optionally in microcrystalline distribution, condensation products of dihaloalkyls such as, for example, dibromobutane with bis-dialkylamines such as, for example, bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol.

Suitable silicone compounds are, for example, dimethyl polysiloxanes, methyl phenyl polysiloxanes, cyclic silicones and amino-, fatty acid-, alcohol-, polyether-, epoxy-, fluorine- and/or alkyl-modified silicone compounds which may be both liquid and resin-like at room temperature. Typical examples of fats are glycerides while suitable waxes are inter alia beeswax, carnauba wax, candelilla wax, montan wax, paraffin wax or microwaxes, optionally in combination with hydrophilic waxes, for example cetostearyl alcohol, or partial glycerides. The pearlescent waxes used may be, in particular, mono- and difatty acid esters of polyalkylene glycols, partial glycerides or esters of fatty alcohols with polybasic carboxylic acids or hydroxycarboxylic acids. Suitable stabilizers are metal salts of fatty acids such as, for example, magnesium, aluminium and/or zinc stearate. Biogenic agents in the context of the invention are, for example, tocopherol, tocopherol acetate, tocopherol palmitate, ascorbic acid, retinol, bisabolol, allantoin, phytantriol, panthenol, AHA acids, plant extracts and vitamin complexes. Suitable antidandruff agents are climbazol, octopirox and zinc pyrethion. Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

In the context of the invention, UV filters are organic compounds which are capable of absorbing ultraviolet rays and of releasing the energy absorbed in the form of longer wave radiation, for example heat. Typical examples are 4-aminobenzoic acid and esters and derivatives thereof (for example 2-ethylhexyl-p-dimethylaminobenzoate or p-dimethylaminobenzoic acid octyl ester), methoxycinnamic acid and derivatives thereof (for example 4-methoxycinnamic acid-2-ethylhexyl ester), benzophenones (for example oxybenzone, 2-hydroxy-4-methoxybenzophenone), dibenzoyl methanes, salicylate esters, 2-phenyl benzimidazole-5-sulfonic acid, 1-(4-tert.butyl-phenyl)-3-(4'-methoxyphenyl)-propane-1,3-dione, 3-(4'-methyl)-benzylidene-bornan-2-one, methylbenzylidene camphor and the like. Other suitable UV filters are finely disperse metal oxides and salts, for example titanium dioxide, zinc oxide, iron oxide, aluminium oxide, cerium oxide, zirconium oxide, silicates (talcum) and barium sulfate. The particles should have an average diameter of less than 100 nm, preferably from 5 to 50 nm and more preferably from 15 to 30 nm. They may be spherical in shape although ellipsoidal particles or other non-spherical particles may also be used. Besides the two above-mentioned groups of primary light filters, secondary light filters of the antioxidant type, which interrupt the photochemical reaction chain initiated when UV radiation penetrates into the skin, may also be used. Typical examples of these secondary light filters are Superoxid-Dismutase, toco-pherols (vitamin E) and ascorbic acid (vitamin C).

In addition, hydrotropes such as, for example, ethanol, isopropyl alcohol or polyols may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols having an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose and aminosugars such as, for example, glucamine.

Suitable preservatives are, for example, phenoxyethanol, formaldehyde solution, parabens, pentanediol or sorbic acid. Suitable insect repellents are N,N-diethyl-m-toluamide, pentane-1,2-diol or Insect Repellent 3535. A suitable self-tanning agent is dihydroxyacetone. Suitable dyes are any of the substances suitable and licensed for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106, These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be prepared by standard cold or hot processes and are preferably produced by the phase inversion temperature method.

EXAMPLES

Example 1

—COOH:—OH Ratio=1.5:1.

906 g (0.19 mole) of a tallow fatty alcohol+100 EO adduct (hydroxyl value 24, 15 mg KOH/g) were introduced into a 1.5 liter stirred reactor and preheated to 90° C. 24 g (0.114 mole) of citric acid monohydrate, 0.65 g of hypophosphorous acid and 4.2 g of methane sulfonic acid were then added. The reaction mixture was heated to 160° C. and a vacuum of 40 mbar was applied. The mixture was stirred for 2 h at that temperature and the pressure was reduced in steps to 5 mbar. The course of the reaction was followed from the acid value and the viscosity of the ester formed as shown in Table 1 below:

TABLE 1

Acid value and viscosity as a function of the reaction time

| Reaction time h | Acid value | Viscosity (5% in water) mPas |
|---|---|---|
| 18 | 7.7 | 2,600 |
| 22 | 7.2 | 3,900 |
| 26 | 7.01 | 4,700 |

Example 2

—COOH:—OH Ratio=2:1.

868 g (0.18 g) of cetyl stearyl alcohol+100 EO adduct were reacted with 31 g (0.148 mole) of citric acid monohydrate, 0.65 g of hypophosphorous acid and 4.2 g of methane sulfonic acid as in Example 1. The course of the reaction was followed from the acid value and the viscosity of the ester formed as shown in Table 2 below:

TABLE 2

Acid value and viscosity as a function of the reaction time

| Reaction time h | Acid value | Viscosity (5% in water) mPas |
|---|---|---|
| 18 | 9.6 | 5,900 |
| 22 | 9.2 | 6,550 |
| 26 | 8.6 | 7,100 |

Example 3

—COOH:—OH Ratio=2.5:1.

820 g (0.4 mole) of cetyl stearyl alcohol+40 EO adduct (hydroxyl value 29, 1 mg KOH/g) were esterified with 74.4 g (0.354 mole) of citric acid monohydrate, 0.59 g of hypophosphorous acid and 3.8 g of methane sulfonic acid as in Example 1. A reaction product with a residual acid value of 17.5 was obtained after 25 h.

Example 4

—COOH:—OH Ratio=2.0:1.

800 g (0.4 mole) of cetearyl alcohol+40 EO adduct were reacted with 58.1 g (0.277 mole) of citric acid monohydrate, 0.57 g of hypophosphorous acid and 3.7 g of methane sulfonic acid as in Example 3. An ester with a residual acid value of 15.1 was obtained after 25 h.

Examples 5 and 6, Comparison Example C1

The thickening effect of the new citric acid esters was tested in a surfactant mixture of alkyl glucosides and ether sulfates. It was determined by the Brookfield method in an RVT viscosimeter (20° C., 10 r.p.m., spindle 1). Formulations F1 and F2 correspond to the invention. PEG-150 Distearate was tested as thickener in comparison formulation F3. The results are set out in Table 3. It can be seen that the esters according to the invention produce a significantly higher viscosity.

TABLE 3

Thickening effect (quantities in % by weight)

| Components | F1 | F2 | F3 |
|---|---|---|---|
| Cocoalkyl oligoglucoside | 20.0 | 20.0 | 20.0 |
| Cocofatty alcohol + 2EO sulfate Na salt | 10.0 | 10.0 | 10.0 |
| Citric acid ester of Example 3 | 3.0 | — | — |
| Citric acid ester of Example 4 | — | 3.0 | — |
| PEG 150 Distearate | — | — | 3.0 |
| Water | | to 100 | |
| Viscosity [mPas] | 18,000 | 21,600 | 3,800 |

What is claimed is:

1. A process for increasing the viscosity of an aqueous surface-active composition comprising adding to the aqueous surface-active composition a viscosity increasing-effective amount of a reaction product of a hydroxycarboxylic acid selected from the group consisting of tartaric acid, malic acid, citric acid and mixtures thereof, and a fatty alcohol polyglycol ether corresponding to formula I:

$$R^1O(CH_2CH_2O)_nH \quad (I)$$

wherein $R^1$ is an alkyl and/or alkenyl group containing from 6 to 22 carbon atoms, and n is a number from 20 to 150, and wherein the reaction product has a Brookfield viscosity of at least 2,000 mPas, as measured using a 5% by weight sample of the reaction product in water.

2. The process of claim 1 wherein the hydroxycarboxylic acid is citric acid.

3. The process of claim 1 wherein in formula I, $R^1$ is an alkyl group having from 16 to 18 carbon atoms and n is a number from 40 to 100.

4. The process of claim 1 wherein the hydroxycarboxylic acid and fatty alcohol polyglycol ether are reacted at a molar ratio of carboxyl to hydroxyl groups of from 1:1 to 3:1.

5. The process of claim 1 wherein the reaction product has an acid value of below 20.

* * * * *